(12) United States Patent
Jaccobson et al.

(10) Patent No.: US 6,750,234 B2
(45) Date of Patent: Jun. 15, 2004

(54) METHODS FOR INCREASING LEPTIN LEVELS USING NICOTINIC ACID COMPOUNDS

(75) Inventors: Elaine Jaccobson, Tucson, AZ (US); Myron Jacobson, Tucson, AZ (US); Hyuntae Kim, Tucson, AZ (US)

(73) Assignees: University of Kentucky Research Foundation, Lexington, KY (US); Arizona Board of Regents on Behalf of University of Arizona, Tuscan, AZ (US)

( * ) Notice: Subject to any disclaimer, the term of this patent is extended or adjusted under 35 U.S.C. 154(b) by 0 days.

(21) Appl. No.: 10/094,063

(22) Filed: Mar. 8, 2002

(65) Prior Publication Data

US 2002/0128298 A1 Sep. 12, 2002

Related U.S. Application Data

(60) Provisional application No. 60/274,349, filed on Mar. 8, 2001.

(51) Int. Cl.[7] ............................................... A61K 31/44
(52) U.S. Cl. ...................... 514/356; 514/355; 514/354
(58) Field of Search ................... 514/356, 355, 514/354, 279, 326

(56) References Cited

U.S. PATENT DOCUMENTS

| | | | | | |
|---|---|---|---|---|---|
| 4,505,896 A | * | 3/1985 | Bernstein | ..................... | 424/705 |
| 4,512,971 A | * | 4/1985 | Wissler | ..................... | 424/85.1 |
| 4,725,609 A | * | 2/1988 | Kull, Jr. et al. | ............. | 514/355 |
| 4,847,260 A | * | 7/1989 | Abe et al. | ................... | 514/279 |
| 4,965,252 A | * | 10/1990 | Kuhrts | ........................ | 514/183 |
| 5,240,945 A | * | 8/1993 | Warshaw | ..................... | 514/356 |
| 5,496,827 A | * | 3/1996 | Patrick | ........................ | 514/310 |
| 5,602,257 A | * | 2/1997 | Zoltewicz et al. | ........... | 546/193 |
| 5,612,382 A | * | 3/1997 | Fike | ............................ | 514/14 |
| 6,326,034 B1 | * | 12/2001 | Mirsky et al. | .............. | 424/725 |

FOREIGN PATENT DOCUMENTS

| | | | |
|---|---|---|---|
| WO | WO98/52927 | * | 11/1998 |
| WO | WO99/59614 | * | 11/1999 |
| WO | WO00/32179 | * | 6/2000 |
| WO | WO00/69426 | * | 11/2000 |

OTHER PUBLICATIONS

Szuecs et al., Treatment of leg ulcer with nicotinic acid, Database CAPLUS, AN 1990:471351, Patent abstract(HU 49485 A2), Oct. 30, 1989.*

Worm et al., The nicotinic acid analogue acipimox increases plasma leptin . . . , European journal of Endocrinology, 2000, vol. 143, pp. 389–395.*

Hoffman et al, Cellular tolerance to adenosine receptor–mediated inhibition of lipolysis . . . , Database CAPLUS, AN 1989:22593 abstract, Endocrinology, 1989, vol. 124(5), pp. 2434–2342.*

* cited by examiner

*Primary Examiner*—Vickie Kim
(74) *Attorney, Agent, or Firm*—Fulbright & Jaworski

(57) ABSTRACT

The invention relates to the use of nicotinic acid and nicotinic acid esters, such as nicotinic acid alkyl esters, to increase the amount of leptin in a subject. As a result, one can treat conditions, such as conditions characterized by wounds, by administering sufficient amounts of nicotinic acid or nicotinic acid ester to increase leptin levels to alleviating amounts. Various conditions and modes of treatment are disclosed.

5 Claims, 6 Drawing Sheets

METHODS FOR INCREASING LEPTIN LEVELS USING NICOTINIC ACID COMPOUNDS

RELATED APPLICATION

This application claims priority of provisional application No. 60/274,349, filed Mar. 8, 2001, incorporated by reference.

FIELD OF THE INVENTION

The invention relates to the use of niacin derivatives and niacin in the regulation of leptin modulated pathways. Specifically, niacin and its derivatives, such as nicotinate esters, lauryl nicotinate ester in particular, stimulate production of leptin, with ramifications as discussed infra.

BACKGROUND AND PRIOR ART

Leptin, a 167 amino acid protein encoded by the ob gene, was identified in the course of research in identifying molecular defects in an obesity prone strain, i.e., the "ob/ob" mouse. It has been found that leptin is produced for the most part in white adipose tissue, with very small amounts being found in brown adipose tissue. Exemplary of the patent literature relating to this molecule are U.S. Pat. Nos. 6,132,724; 6,124,448; 6,124,439; 6,068,976; 6,048,837 and 5,795,909, all of which are incorporated by reference.

The first reports on leptin suggested that it was an adipocyte derived, signaling molecule, which limited food intake and increased energy expenditure, i.e., an "adiposat." The evidence supporting this included observed decreases in body weight, and improved metabolic control in rodents that evidenced genetic or diet induced obesity that were injected with leptin. In the case of ob/ob mice, which have mutations in the ob gene, leading to synthesis of defective leptin molecules that are degraded intracellularly, the effect of leptin is especially pronounced. The ob/ob mice are obese, diabetic and sterile, and exhibit reduced activity, metabolism, and body temperature. In addition, leptin-deficient ob/ob mice suffer from seriously delayed wound healing. Systemic or topically administered leptin has been shown to improve re-epitheliazation of wounds in this model. See Frank, et al., J. Clin. Invest. 106: 501–509 (2000). As such, the ob/ob mouse has been used as a model system for testing drugs for their ability to reverse impaired wound healing.

In addition to the effect on leptin deficient mice, discussed supra, leptin markedly promoted re-epitheliazation in wild type mice. In addition, STAT 3 and peroxisome-proliferator activated receptor ("PPAR" hereafter), which are the downstream regulators in the leptin pathway, are involved in skin homeostasis. See Komuvres, et al., J Invest. Dermatol 115:361–267 (2000). STAT 3 has been shown to play an essential role in skin remodeling, including hair follicle cycling and wound healing. It is also known that PPARα activators normalize cell proliferation, including epidermal differentiation, and accelerate the development of the epidermal permeability barrier. See Hanley, et al., J. Clin Inv. 100:705–712 (1997). Recently, it has been demonstrated that PPARα activators inhibit murine skin tumor promotion. This is consistent with PPARα having a role in skin physiology. See Thuillier, et al., Mol. Carcinogenesis 29:134–142 (2000).

Further research on leptin has revealed that the molecule alters the transcription of several adipose specific genes involved in lipogenesis, lipolysis, and energy metabolism. It also appears to trigger apoptosis in white adipose tissue. Most of the molecule's metabolic effects appear to result from specific interactions with receptors located in the central nervous system, and in peripheral tissues. The receptor has been identified and is a Class I cytokine receptor that belongs to a family that includes the IL-2 receptor, interferon receptor and growth hormone receptor. In brief, the leptin receptor transmits leptin signal to the three STAT molecules STAT 3, 5, and 6, referred to collectively as the "fat-STATS."

The accepted view of leptin is that its primary role is to prevent obesity via regulating food intake and thermogenesis via action on hypothalomic centers. Recent evidence suggests, however, that leptin may have an additional role, i.e., it may exhibit antisteatotic activity, in that fatty acid over-accumulation in non-adipose tissue may be prevented by leptin mediated regulation of β-oxidation. Leptin increases enzymes involved in fatty acid oxidation and stimulates a previously unobserved form of lipolysis, where glycerol is released without proportional release of free fatty acids.

Various leptin receptor isoforms are expressed throughout the body suggesting that leptin has additional physiological functions on extra-neural tissue. Studies have been carried out to evaluate tissue responsiveness to leptin, via determining what effects, if any, it has on glucidic and lipidic metabolism, as well as expression of some enzymes. If a direct effect of leptin on a given tissue is observed, it implies rapid induction of signal transduction mechanisms, flowing from hormone/receptor binding. Essentially the mechanism of action can be summarized as follows: leptin activates STAT 3 in adipose tissue, binding of leptin to its receptor leads to receptor oligomerization, and JAK activation, leading in turn to STAT phosphorylation; phosphorylated STATS dimerize and translocate into nuclei, where they activate target genes. In brief:

(i) Leptin activates STAT 3, and increases PPARα activity;

(ii) PPARα/PPRE induces apo A-I expression in liver cells;

(iii) STAT3/PPARα is essential for skin homeostasis;

(iv) PPARα activators inhibit mouse skin tumor promotion.

See, e.g. Bendinelli, et al., Mol. Cell Endocrin 168:11–20 (2000); Unger, et al., Proc. Natl. Acad. Sci USA 96:2327–2332 (1992); Peters, et al., J. Biol. Chem. 272:27307–27312 (1997); Hanley, et al., J. Clin. Invest. 100:705–712 (1997); Sano, et al., EMBOJ 18:4657–4666 (1999); Thuillier, et al., Mol. Carcin 29:134–142 (2000).

In addition to playing a role in energy regulation, leptin also regulates endocrine and immune functions. Leptin levels increase acutely during infection and inflammation, and may represent a protective component of the host response to inflammation. Leptin deficiency increases susceptibility to infectious and inflammatory stimuli and is associated with dysregulation of cytokine production. See Faggioni, et al., FASEB J. 15:2565–2571 (2001).

In addition, it can be hypothesized that the pathway described supra can also lead to skin homeostasis and remodeling, which in turn leads to epidermal barrier development, wound healing, and hair growth, as well as the inhibition of skin tumor promotion caused by increased immune functions. This is summarized in FIG. 1.

Niacin is essential to formation of the coenzymes nicotinamide dinucleotide (NAD), and NAD phosphate (NADP), where the nicotinamide moiety acts as an electron acceptor or hydrogen donor in many biological redox reactions. To elaborate, NAD functions as an electron carrier for intracellular respiration, and as a coenzyme in the oxidation of fuel molecules. NADP acts as a hydrogen donor in reductive biosynthesis, including fatty acid and steroid synthesis. As is the case with NAD, it also acts as a coenzyme.

NAD is the substrate for three classes of enzymes that transfer ADP-ribose units to proteins involved in DNA repair, cell differentiation, and cellular calcium mobilization. Nicotinic acid, in contrast to nicotinamide, when given in doses of 1.5–4 g/day improves blood cholesterol profiles.

Acipimox, a commercially available, nicotinic acid analog and hypolipodemic agent, was shown to increase plasma leptin levels in transgenic mice. See, e.g., Worm, et al., Eur. J. Endocrin 143:389–395 (2000).

It has been shown that nicotinic acid derivatives have efficacy in, inter alia, skin cell protection, DNA repair, etc. See, e.g., U.S. Pat. No. 6,337,065, filed Dec. 1, 1999 to Jacobson, et al., incorporated by reference in its entirety. This application describes various nicotinic acid derivatives, including a dodecyl, or lauryl nicotinic acid ester. It has now been found that such nicotinic acid esters, such as lauryl nicotinic acid ester, stimulate leptin production to an extent not seen with niacin. As the nicotinic acid esters can be formulated as e.g., materials suitable for topical application, a new approach to leptin stimulation and production is provided.

DETAILED DESCRIPTION OF PREFERRED EMBODIMENTS

EXAMPLE 1

Adipose tissue is recognized as the major source of leptin production in animals. As such, experiments were designed to determine the effect of niacin on leptin production in adipocytes.

Human adipocytes were obtained in accordance with standard methods. In brief, preadipocytes were collected from subcutaneous adipose tissue, following collagenase treatment. The preadipocytes were plated, and allowed to differentiate for 3 weeks, to form adipocytes.

The adipocytes were then incubated, in 0.6 ml of DMEM/F-10 medium, to which 2% bovine serum albumin was added. In addition, cultures either received 0.1 mM niacin, or did not.

After 24 hours, the culture medium was analyzed for leptin, using a commercially available ELISA kit.

Figure 2:
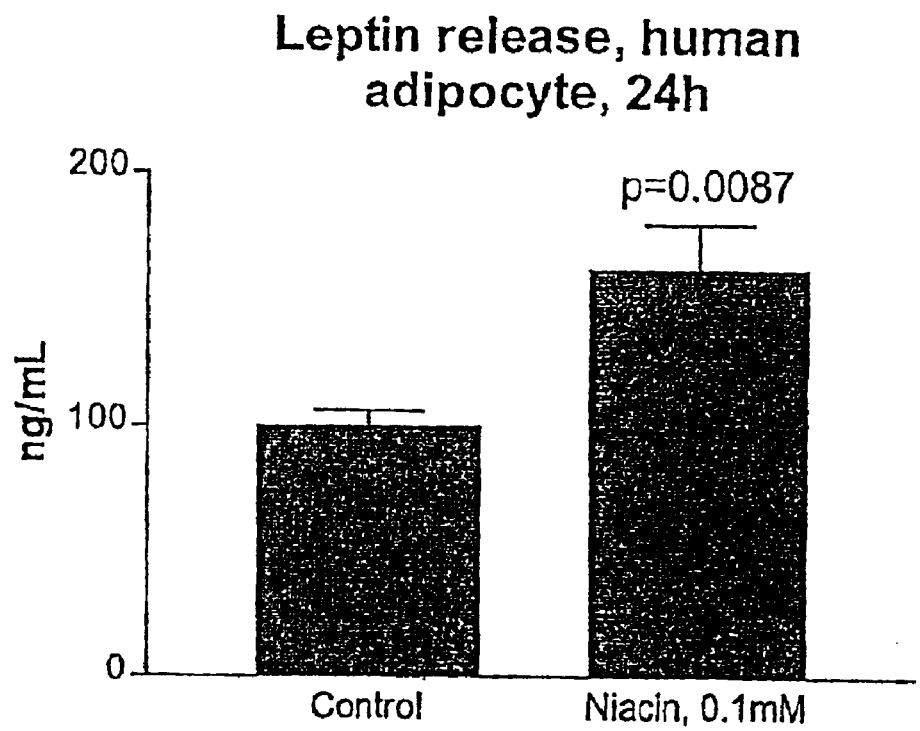
FIG. 2 summarizes data relating to leptin production in adipocytes in vitro.

The results, which are presented in FIG. 2, show that in the cultures to which niacin was added, leptin production increased 62%.

EXAMPLE 2

Female apoB/CETP double transgenic mice, obtained from a commercial supplier, were divided into 3 groups, and housed as six animals per cage. One group served as control, and received a standard diet, without added niacin. Backs were shaved, and lotion was applied which was identical to the lotion applied to the third group, as described infra, without lauryl nicotinate ester. A second group received niacin, in the form of its sodium salt, dissolved in drinking water at a concentration of 0.75% (0.63% free acid). The niacin intake of the animals was estimated based on water consumption and was approximately 1400 mg/kg of body weight, based upon an estimated consumption of 23 ml of water per 100 g of body weight, and an average body weight of 25 g. This is equivalent to about 8.4 g/day for a 70 kg human. See Freireich, et al., Cancer Chemother. Rep. 50: 219–244 (1966) incorporated by reference. For the third group, backs were shaved, and the lauryl nicotinate ester was applied to shaved areas, via 200 mg of lotion, containing 10% (wt/wt) of the lauryl nicotinate ester. The amount of the ester applied is approximately 80–800 mg/kg, again assuming an average weight of 25 g. Using Freireich, supra, this is equivalent to a dose from about 0.48 to about 4.8 g/day/70 kg human. The lotion was applied daily for 13 weeks.

Figure 3:
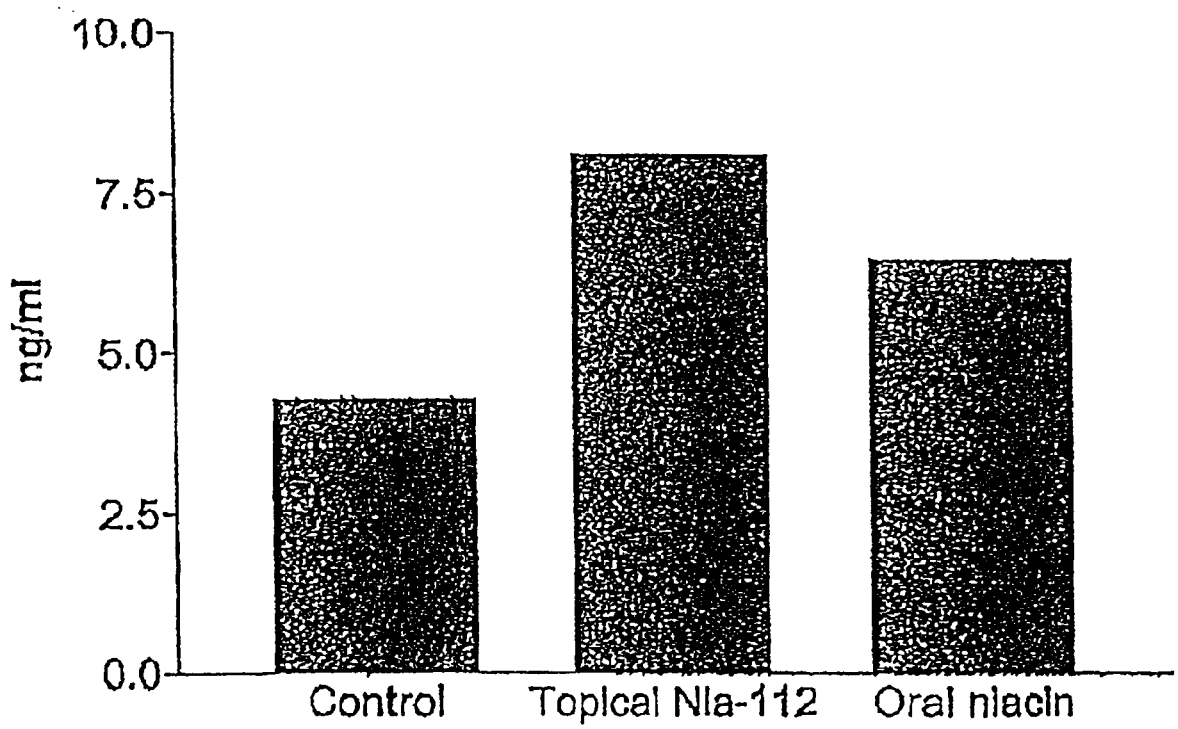
FIG. 3 compares the result of experiments designed to determine the levels of plasma leptin in test animals, after niacin was administered in the form of lauryl nicotinic acid ester.

Leptin levels in plasma were determined using a commercially available murine leptin radioimmunoassay. The RIA was carried out on fasting (16 h) blood samples obtained from the retroorbital plexus. The blood samples were collected and centrifuged at 2000×g for 15 minutes to secure plasma. The results, summarized in FIG. 3, show that oral niacin did increase the amount of circulating leptin, however, the lauryl nicotinate ester surpassed it in terms of the amount of circulating leptin.

EXAMPLE 3

The experiments described in example 2 were continued, in the experiment described in this example. Specifically, male BALB/C mice were shaved, from the scapulae to tail bases. The subject animals then received topical application of the lauryl nicotinate ester lotion, described in example 2, supra, or myristyl nicotinate ester lotion, in varying concentrations. Controls received vehicle only. The lotion was applied at a dose of 4 ml/kg/mouse.

Figure 4:
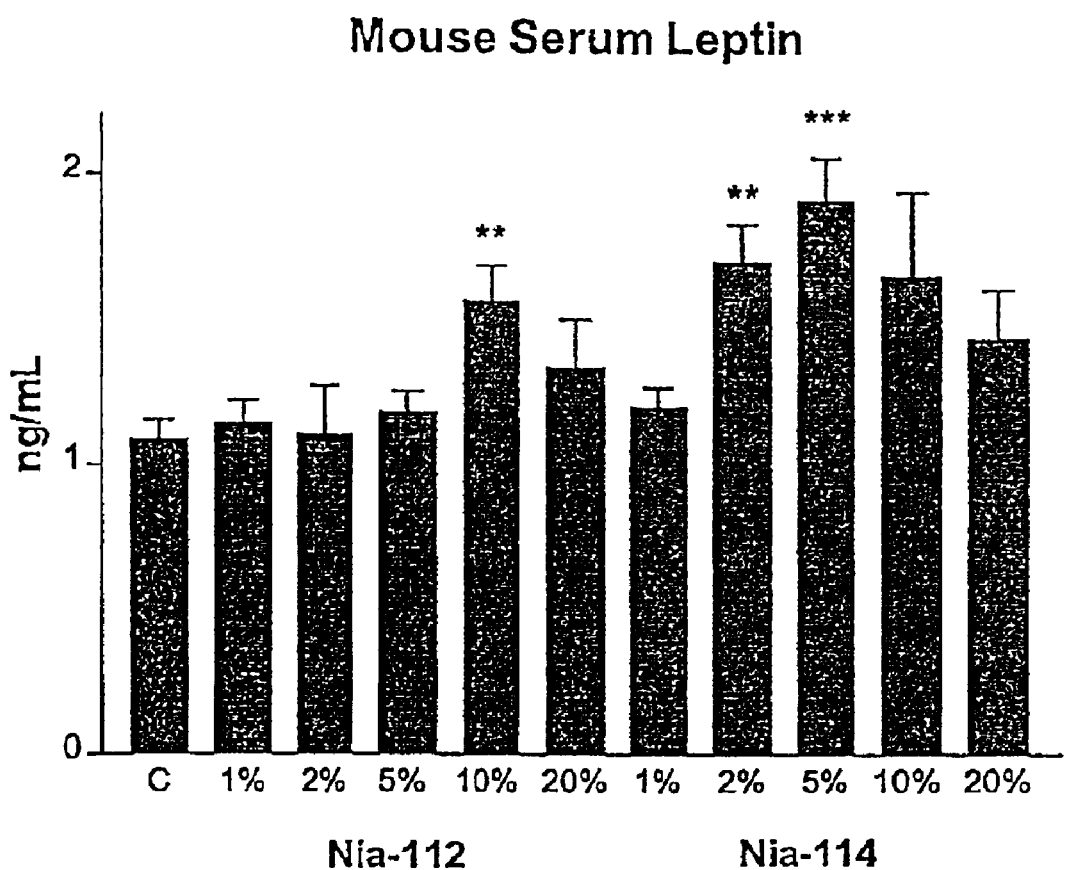
FIG. 4 presents a summary of data generated following the work of example 2, in which serum leptin levels were measured. "NIA 114" is the lauryl ester, while "NIA 112" is the myristyl ester.

Serum leptin levels were measured, as described, supra. The results indicate that the serum leptin levels increased by 45% in the subject animals which received the 10% lauryl nicotinate ester lotion, while the increase for subject animals which received myristyl nicotinateesterwas 57% (for the 2% formulation), and 77% (for the 5% formulation). FIG. 4 presents these results.

EXAMPLE 4

The association of leptin with wound healing was discussed supra. This correlation was investigated in these experiments.

Mice were inflicted with full thickness wounds of about 6 mm in diameter, under anesthesia (sodium phenobarbital). They then received topical application of a 20% nicotinate ester lotion, every day, for 14 days. The dosing was 100 µl for each application, with two applications every day. As a control, the lotion without the ester was used. Wound diameter was measured every day.

Figure 5:
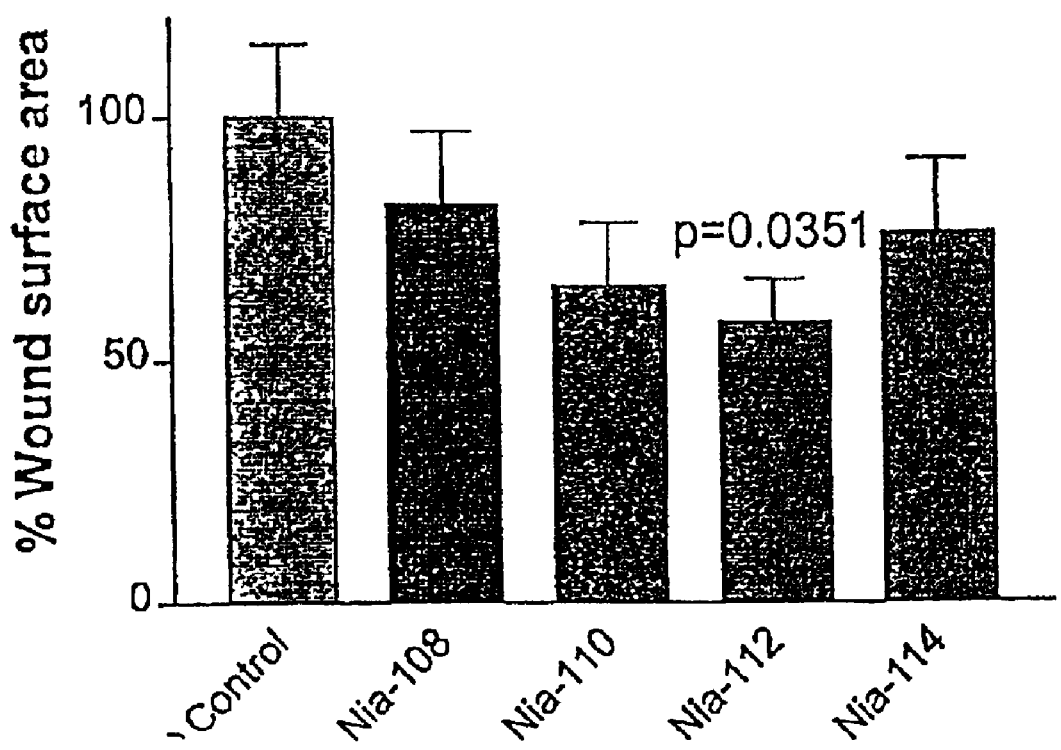
FIG. 5 summarizes results of experiments designed to show changes in wound size following administration of the nicotinic acid esters.

The results are presented in FIG. 5, which shows that the mice which received the nicotinate ester containing formulations showed a reduction of wound thickness, as composed to controls. The lauryl ester was most effective with a 43% reduction.

Figure 6:
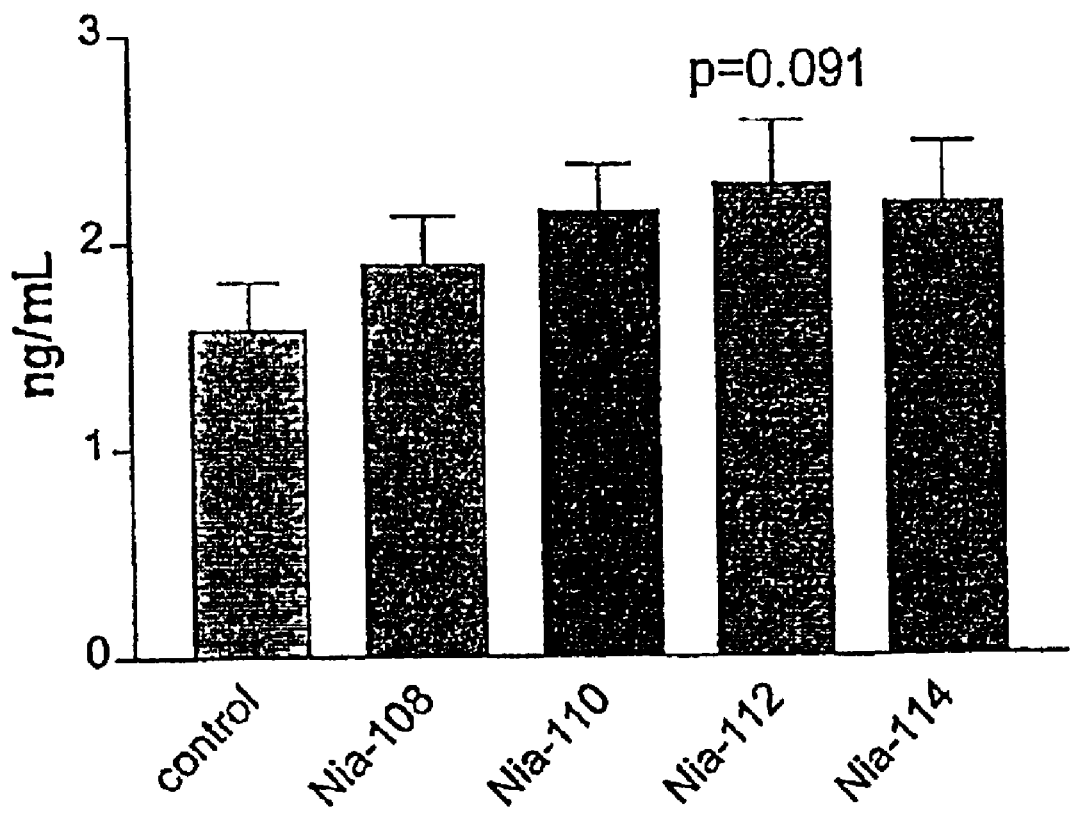
FIG. 6 sets forth parallel results, in which the serum leptin levels of the mice were measured.

When the serum leptin levels were measured, the mice which received the nicotinate ester application were found to have an increase of 44% as compared to controls. These results are depicted in FIG. 6.

Figure 1:
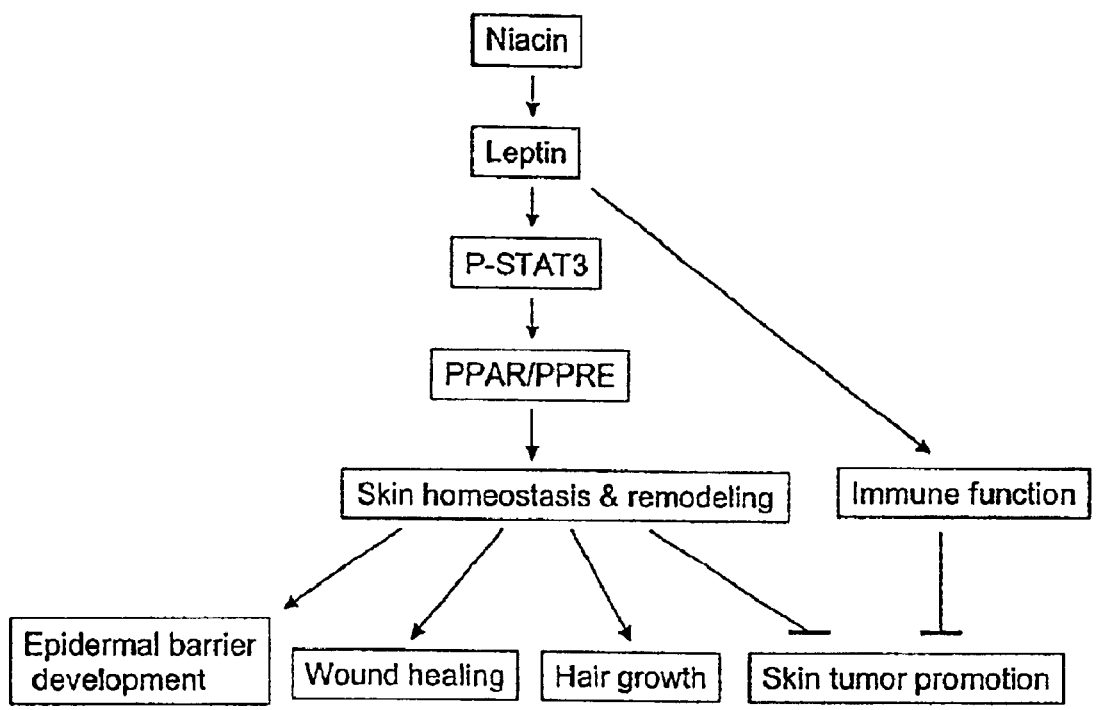
FIG. 1 is a proposed mechanism and effect pathway believed to operate in the invention. Note a flat line means the target condition is inhibited. Hence, the effect of leptin on skin tumor promotion is inhibition of the tumor.

The foregoing examples set forth various features of the invention which include, inter alia, a method for stimulating production of leptin in a subject in need thereof, by administering to said subject a leptin stimulating amount of a nicotinic acid or nicotinic acid derivative, such as a nicotinic acid ester. Most preferably, this is a lauryl nicotinic acid ester, although other compounds, such as those described in the patent application cited supra may also be used. Especially preferred are nicotinic acid per se, or nicotinic acid alkyl esters, where the ester moiety contains from 1–30, optionally substituted, carbon atoms. More preferably, the alkyl moiety contains 1–22 carbon atoms, most preferably 1–18 carbon atoms. The subjects are preferably subjects suffering from a condition that can be alleviated by increased leptin levels, including those set forth in FIG. 1, improved immune function, skin epithelation, hair follicle cycling, inhibition of tumor formation, such as skin tumor formation, and so forth.

The mode by which the nicotinic acid or ester is administered to the subject may vary. Oral, time release, intravenous, intradermal, and other forms of administration are contemplated, as topical administration. Such topical administration may be via a creme, lotion, liquid, aerosol, body wash, mouthwash, toothpaste, gavage, or other form of topical administration. For example, in the case of timed released application, "patches," such as the type used in timed release of nicotine, bandages, wraps, and so forth may be employed.

The nicotinic acid ester is administered in an amount sufficient to stimulate leptin production. The dose used can and will vary; however, formulations should deliver, e.g., doses ranging from about 0.1 to about 10 g/day/70 kg body weight, more preferably from about 0.1 to about 7 g/day/70 kg body weight, most preferably from about 0.4 to about 5/g/day/70 kg body weight.

As indicated, supra, the stimulation of leptin production can lead, in addition to the effects associated with leptin previously, to regression of skin tumors, skin homeostases and remodeling, epidermal barrier development, wound healing, and hair growth.

Other applications will be clear to the skilled artisan and need not be elaborated herein.

We claim:

1. A method for increasing leptin levels in a subject suffering from a full thickness wound comprising administering to said subject an amount of a nicotinic acid alkyl ester sufficient to increase leptin levels in said subject so as to reduce thickness of said full thickness wound, wherein the alkyl chain of said nicotinic acid alkyl ester contains from 8 to 22 carbon atoms.

2. The method of claim 1, wherein said alkyl chain contains 12 or 14 carbon atoms.

3. The method of claim 1, wherein said nicotinic acid alkyl ester is administered orally.

4. The method of claim 1, wherein said nicotinic acid alkyl eater is administered topically.

5. The method of claim 1, comprising administering more than one nicotinic acid alkyl ester.

* * * * *